United States Patent [19]

Alvarado-Urbina et al.

[11] 4,404,368

[45] Sep. 13, 1983

[54] LYOPHILIZED PHOSPHORYLATED NUCLEOSIDES

[75] Inventors: Gabriel G. Alvardo-Urbina, Nepean, Canada; Kelvin K. Ogilvie, Candian, Canada

[73] Assignee: ens Biologicals Inc., Toronto, Canada

[21] Appl. No.: 234,788

[22] Filed: Feb. 17, 1981

[51] Int. Cl.³ .................... C07H 19/20; C07H 19/10
[52] U.S. Cl. ...................................... 536/27; 536/28; 536/29
[58] Field of Search ............................ 536/27, 28, 29

[56] References Cited

U.S. PATENT DOCUMENTS 3,338,882  8/1967  Wechter ............................. 536/29
3,433,782  3/1969  Kreiser ............................. 536/27

OTHER PUBLICATIONS

Letsinger, R., and Lunsford, W., J. Am. Chem. Soc., vol. 90, pp. 3655–3661, 1976.
Matteucci, M. and Caruthers, M., Tetrahedron Letters, vol. 21, pp. 719–722, 1980.
Letsinger, R., J. Am. Chem. Soc., vol. 97, pp. 3278–3279, 1975.
Fieser, L. et al., "Reagents for organic synthesis", vol. 1, p. 333, 1967.

*Primary Examiner*—Blondel Hazel
*Attorney, Agent, or Firm*—Murray and Whisenhunt

[57] ABSTRACT

Phosphorylated nucleotides for addition to nucleotide chains in the stepwise synthesis of oligonucleotides, e.g. as a polymeric support, are prepared in dioxane solvent and then lyophilized, to provide a stable, dry product ready for re-dissolving in reaction solvent. The lyophilized products are stable indefinitely and do not suffer from decreased reactivity.

5 Claims, No Drawings

LYOPHILIZED PHOSPHORYLATED NUCLEOSIDES

FIELD OF THE INVENTION

This invention relates to oligonucleotides, and processes for their preparation, and more particularly to intermediate reagents for use in synthesis of oligonucleotides.

BACKGROUND OF THE INVENTION

Oligonucleotides, i.e. compounds consisting of from about 4 to about 100 nucleotide units linked together to form a nucleotide chain, are effectively portions of nucleic acids eg. the biologically and genetically important deoxyribonucleic acids (DNA) and ribonucleic acids (RNA). Thus they constitute biologically important products, e.g. as genes. Synthesis of oligonucleotides with exact, predetermined sequences of units in the chain provides materials capable of being spliced into natural nucleic acids in living organisms, e.g. to replace defective natural genetic material or to modify a living cell so as to provide it with the capability to produce useful secretory products on an enhanced scale. For example, insulin-producing genes, synthetic oligonucleotides of correct unit sequence, have been synthesized and introduced into appropriate cells, to enhance insulin production thereby.

It is however necessary to provide reliable, economical processes for producing oligonucleotides, if such production procedures are to assume commercial significance. Synthetic oligonucleotides must be carefully prepared, in step-wise, controlled fashion, to ensure the production of a material with the exactly predetermined unit sequence in its chain. The presence of erroneous chain sequences, omission of a unit from its proper position along the oligonucleotide chain and similar, apparently minor defects, can have potentially disastrous consequences, since the unit sequences in the chain carry the information determining the nature of the secretory products and other behaviour of the cell into which it has been introduced.

One promising method for producing oligonucleotides of predetermined sequence is the polymer support synthesis, described in U.S. patent application Ser. No. 6,149,685, of Ogilvie and Bender, filed May 14, 1980. In this method, a solid polymer such as silica gel is derivatized to put functional side groups thereon, and the polymer is reacted with a first, appropriately protected nucleoside unit, to bond that unit to the solid polymer "support". Then, after suitable deprotection of the linked unit, it is reacted with an appropriate preformed phosphorylated nucleotide compound, which links to the appropriately deprotected location on the polymer-supported unit and hence is added to the nucleotide chain. By repeating the sequence of operations, a nucleotide chain can be built up of substantially any desired length, and with predetermined unit sequences. As a final or close to final step, the oligonucleotide chain is cleaved from the polymer and isolated.

A particular advantage of the above-described process is that it provides the possibility of semi-automatic operation. The polymer-supported product, which is solid, can be kept in a single reaction vessel such as a column throughout the operations, and the various reagents, solvents and wash liquids added thereto from storage vessels of programmed sequence and for pre-set durations. The nucleotide reagents for addition to the growing nucleotide chain are only a total of four in number (for a DNA-type chain or an RNA-type chain, although not the same four in each case). They can be prepared ahead of time, ready for addition to the polymer-supported intermediate product, stored in reagent vessels, and fed to the reaction column as and when required.

In this and similar processes, therefore, the preformed polyphorylated nucleotide compounds provide key reagents. They may correspond in general to the formula

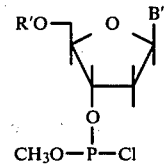

where R′ represents a protecting group for the 5′-hydroxyl and B′ represents the base group. The chlorine group is available for reaction with a hydroxyl or another unit, for chain extension purposes. Such compounds are comparatively easy to prepare, but are not very stable.

It would greatly simplify and enhance the economics of the aforementioned and other oligonucleotide preparation processes if phosphorylated nucleotide compounds could become a commodity product, available from central manufacturing sources. However, at present their lack of adequate stability precludes this. They must effectively be prepared as and when required for use in oligonucleotide synthesis, which requires their preparation on site. They are normally too unstable to permit their preparation, storage and transportation prior to use. To have to store and ship the reagents under special conditions to prevent deterioration thereof, or to react the reagents chemically so as to protect their reactive sites and prevent deterioration thereof, is clearly undesirable, as adding additional process steps or apparatus features to the synthesis as a whole.

SUMMARY OF THE INVENTION

It has been found that, provided a correct choice of solvent is made, nucleotide compounds for use in the aforementioned polymer-support synthesis process, can be lyophilized and stored in their freeze dried condition, without significant deterioration or loss of reactivity, for extended periods of time. The appropriate solvent is dioxane.

Thus according to a first aspect of the present invention, there is provided stable, lyophilized, phosphorylated nucleotide compound of general formula I:

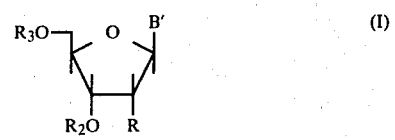

where R is hydrogen, protected hydroxyl or a halophosphite group

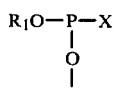
(II)

in which X is fluorine, chlorine, bromine or iodine and $R_1$ is a chemical protecting group for hydroxyl; $R_2$ and $R_3$ are independently selected from hydrogen, chemical protecting groups for hydroxyl and halophosphite group $R_1$—O—P—X, with the proviso that one of R, $R_2$ and $R_3$ is a halophosphite group, said lyophilized nucleotide compound being readily soluble in pyridine at room temperatures.

According to a second aspect of the present invention, there is provided a process for preparing lyophilized phosphorylated nucleotides of general formula I given above, which comprises forming a solution of said nucleotide in dioxane solvent, subjecting the solution to low pressure conditions to cause sublimation of the dioxane solvent, and recovering lyophilized nucleotide compound of formula I, in light, divided form, readily soluble in pyridine at room temperatures.

As a result of extensive screening, it has been established that the lyophilized nucleotide compounds of the present invention can only be prepared through the use of dioxane solvent. Indeed it was believed impossible to prepare freeze dried nucleotide compounds, with substantially unimpaired reactivity and ready solubility in suitable condensation solvents such as pyridine for chain extension reaction to prepare polynucleotides, until the use of dioxane solvent was conceived. Dioxane has the ability to dissolve the nucleotide compounds easily and readily at room temperature without apparently exerting any adverse effects thereon, chemically or physically. Dioxane has a high latent heat of evaporation. The solution of nucleotide in dioxane can be cooled to solidification, subjected to high vacuum, and the dioxane sublimed off in toto, all without adverse effects on the nucleotide compound. The solid nucleotide compound is recovered in a typical freeze dried physical form, namely, light fluffy discrete particulate form, as opposed to a heavy granular powder or mass. In this condition, the nucleotide compound can be stored indefinitely and transported, taking only normal precautions such as moisture exclusion and contamination etc. The compounds readily re-dissolve in appropriate solvents for the carrying out of additional reaction processes with them.

DESCRIPTION OF THE PREFERRED EMBODIMENTS

Dioxane is, in addition, an eminently suitable solvent in which to conduct the preparative reactions for preparing the phosphorylated nucleotide reagents for lyophilization. This reaction is conducted by treating a nucleoide compound having an unprotected hydroxyl group at the position through which subsequent chain extension is to be effected, with a phosphodihalidite compound. It is therefore preferred according to the invention to prepare the nucleotide compounds by condensation in dioxane solvent, and then to lyophilize the dioxane solution product so obtained, to remove the dioxane therefrom by sublimation and leave stable, low density lyophilized phosphorylated nucleotide compound ready for storage and further use.

Thus according to a preferred embodiment of the present invention, there is provided a process for preparing lyophilized phosphorylated nucleotide compounds of general formula I given above, which comprises reacting, in liquid solution in dioxane, a nucleotide compound of general formula (III)

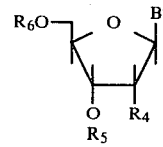
(III)

wherein $R_4$ is hydrogen, hydroxyl or chemically protected hydroxyl; $R_5$ and $R_6$ are independently selected from hydrogen and hydroxyl protecting groups, with the proviso that only one of $R_4$, $OR_5$ and $OR_6$ represents hydroxyl, and B' has the same meanings as in formula I, with a phosphodihalidite compound of formula $X_2.PO.R_7$ where X is fluorine, chlorine, bromine or iodine, and $R_7$ is lower alkyl, to form a compound of general formula I above, and subjecting the reaction solution so formed to cooling and low pressure conditions to sublime off the dioxane solvent, and recovering dry, stable lyophilized nucleotide product of formula I.

The present is applicable to both deoxyribonucleotides and ribonucleotides. It will be appreciated that, when $R_4$ in formula III or R in formula I represents hydrogen, the unit is a deoxyribose unit. When $R_4$ or R is hydroxyl or protected hydroxyl, the unit is a ribose unit. Oligonucleotides may be prepared, using processes and products of this invention, as deoxyribonucleotide chains or ribonucleotide chains, or mixtures of units thereof. In the deoxyribonucleotide units, base B' is adenine, guanine, cytosine or thymine. In ribonucleotide units, the base B' is adenine, guanine, cytosine or uracil. While in most cases the present invention will involve such base units in their normal, unmodified arrangements, it will be appreciated that compounds having modified or substituted such moieties are within the scope of the present invention, since such changes do not affect the basic nature of the process and products of this invention.

In preparing the compounds of formula I ready for the lyophilization step, it is preferred to react the compound of formula II with phosphodichloridite, $X_2.PO.CH_3$ i.e. a phosphodihalidite as aforementioned in which X is chlorine and R is methyl. Clearly other halogens and other lower alkyl groups can be used. However, the reaction between suitable protected nucleotide compounds and phosphodichloridite is well known in nucleotide chemistry (see Letsinger & Lunsford, J. Am. Chem. Soc. 98, 6190, 1970, for example) so that this is preferred. Its method and appropriate conditions are well known and do not require detailed description herein. Generally it is conducted in an aprotic mildly basic liquid solvent in the presence of a suitable catalyst such as collidine or the like. In the present invention, as noted, dioxane is used. A wide variety of other solvents are known and suitable for use in this condensation reaction, but only dioxane is suitable for both the condensation reaction and the subsequent freeze drying.

In the standard way, the nucleotide compounds for reaction with dichloridite, and the resulting freeze dried nucleotides to be added to a growing oligonucleotide chain, should be appropriately protected to ensure reaction at the right location on the molecule. Deoxyribose units have hydroxyl groups at the 3' and 5' positions. It is preferred in the present invention to protect the 5'-hydroxyl and hence add the phosphite moiety at the 3'-position. This is most suitable when the chain is to be extended through 3', 5' linkages from a polymer support. In the use of ribose units, there are hydroxyls at the 2', 3' and 5' positions, two of which should be protected to arrange the desired halo-phosphite reaction. Hydroxyl protecting groups are standard, well known and commonly used in nucleotide chemistry, for ensuring desired locations of reactions, and the individual protection reactions and groups to be used will be apparent to those skilled in this art. Examples of suitable protecting groups for use as $R_2$, $R_3$, $R_5$, $R_6$ and, with an intermediary oxygen group, R and $R_4$, include lower alkyl (methyl, ethyl, propyl, isopropyl, butyl, etc.) phenyl, benzyl, silyl, lower alkyl silyl, tert butyl dimethyl silyl, trityl, monomethoxytrityl, dimethoxy trityl and the like, as known. The phosphorylation reaction proceeds rapidly, at room temperatures, to yield a solution of the phosphorylated nucleotide in dioxane.

Then the resulting solution is lyophilized. This is accomplished by known techniques and according to readily discernible conditions having regard for the known physical properties of the dioxane solvent (boiling point at atmospheric pressure 101.1° C. at 20 mm pressure 12° C.; melting point 11.8° C.). Conveniently the temperature of the solution is held at $-30°$ C., and pressure reduced sufficiently to sublime off the solvent and leave the product in a dry solid fluffy particulate form generally typical of freeze dried materials.

The product so obtained is stable and easy to handle. It should of course be kept free from moisture and other contaminants. It will readily and easily dissolve at room temperatures in appropriate solvents for conducting the subsequent chain extension condensation steps (normally pyridine, tetrahydrofuran or dioxane), to prepare stock solutions thereof for oligonucleotide preparation, at suitable concentrations. Its reactivity in such condensation reactions is not significantly affected by its having undergone lyophilization. The lyophilized product can be stored indefinitely and transported and shipped, in its dry lyophilized form, without significant deterioration.

The invention is further illustrated in the following specific examples.

EXAMPLE 1

1 mmole of adenine deoxyriboside, protected at its 5'-position with monomethyoxytrityl MMT , was dissolved in 3 ml dioxane. The resulting solution was added dropwise to a room temperature solution of methyldichlorophosphite (90 ul) in 3 ml dioxane containing 660 ul of collidine (in a 15 ml vial). Reaction took place substantially instantaneously, to give a solution of 5-protected adenine deoxyriboside-3'-methyl-chlorophosphite.

The reaction solution so formed was kept in the initial reaction vessel and the temperature lowered to and maintained at $-30°$ C. in a dry ice/isopropanol cooling bath, and lyophilized overnight (>8 hours) in a lyophilizer under at least 0.5 Torr. The product was left in the vial in the form of a fluffy, dry, particulate solid material.

After storage in this condition for an extended period of time, the lyophilized phosphorylated nucleotide product was dissolved in dry pyridine (1 m M in 50 mls pyridine) at room temperature, without difficulty, and was found to form a solution stable for one week. The solution was added to a reaction column, at a flow rate of 5 ml/minute, in which was contained a solid derivatized silica gel polymer having linked thereto a nucleotide dimer (G,T) with free hydroxyl at the end 5'-position. Reaction took place at room temperature. The nucleotide coupled to the nucleotide dimer to form a polymer supported nucleotide trimer, in a yield comparable to that obtained by using freshly prepared phosphorylated protected nucleotide (>90%).

EXAMPLE 2

Essentially similar results to those reported in Example 1 were obtained using 5'-protected cytosine deoxyriboside, guanine deoxyriboside and thymine deoxyriboside. All were phosphorylated with methyldichlorophosphite, in dioxane, and lyophilized therefrom to yield solid, fluffy stable product which was subsequently dissolved in pyridine and used to chain extend a 3'-unprotected, polymer supported oligonucleotide chain.

EXAMPLE 3

Following the procedure of Example 1, 1 m mole of cytosine riboside, protected at its 2'-position and at its 5'-position with MMT, was dissolved in 3 ml dioxane, reacted with methyldichlorophosphite and the resultant product lyophilized. The dry fluffy product so obtained was stored, then dissolved in pyridine and reacted with a polymer-supported pentamer of ribonucleotide units, with the terminal 5'-position thereof unprotected. The previously lyophilized product coupled to the oligomer in approximately 90% yield, comparable to that generally obtained with non-lyophilized product.

Similar results are obtained in respect of adenine, riboside, guanine riboside and uracil riboside.

We claim:

1. A process for preparing lyophilized phosphorylated nucleotides of general formula 1

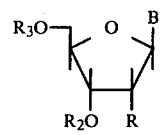
I where R is hydrogen, oxy-lower alkyl, oxyphenyl, oxybenzyl, oxysilyl, oxy-lower alkylsilyl, oxytrityl, oxy-loweralkoxytrityl or a halophosphite group

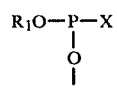
II in which
X is fluorine, chlorine, bromine or iodine and $R_1$ is a chemical protecting group for hydroxyl and selected from lower alkyl, phenyl, benzyl, silyl, lower alkylsilyl, trityl and lower-alkoxytrityl;
$R_2$ and $R_3$ are independently selected from hydrogen, lower alkyl, phenyl, benzyl, silyl, lower alkyl silyl, trityl, lower-alkoxytrityl and halophosphite group $R_1O-P-X$ with the proviso that one of R, $R_2$ and $R_3$ is a halophosphite group;
B' is a base selected from guanine, adenine, uracil, cytosine and thymine;

which comprises forming a solution of said nucleotide in dioxane solvent, subjecting the solution to low pressure conditions to cause sublimation of the dioxane solvent, and recovering lyophilized nucleotide compound of formula 1 in light, divided form, readily soluble in pyridine at room temperatures.

2. A process for preparing lyophilized phosphorylated nucleotide compounds of general formula I given in claim 1, which comprises reacting, in liquid solution in dioxane, a nucleoside compound of general formula (III)

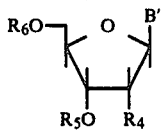

(III)

wherein $R_4$ is hydrogen, hydroxyl, oxy-lower alkyl, oxyphenyl, oxybenzyl, oxysilyl, oxy-lower alkylsilyl, oxytrityl and oxy-loweralkoxytrityl; $R_5$ and $R_6$ are independently selected from hydrogen lower alkyl, phenyl, benzyl, silyl, lower alkylsilyl, trityl and lower alkoxytrityl, with the proviso that only one of $R_4$, $OR_5$ and $OR_6$ represents hydroxyl, and B' has the same meanings as in formula I, with a phosphodihalidite compound of formula $X_2.PO.R_7$ where X is fluorine, chlorine, bromine or iodine, and $R_7$ is lower alkyl, to form a compound of general formula I above, and subjecting the reaction solution so formed to cooling and low pressure conditions to sublime off the dioxane solvent, and recovering dry stable lyophilized nucleotide product of formula I.

3. The process of claim 2 wherein the phosphodihalidite compound is methyldichlorophosphite, of formula $CH_3-PO-Cl_2$.

4. The process of claim 3 wherein $R_4$ and $R_5$ represent hydrogen and $R_6$ is selected from lower alkyl, phenyl, benzyl, silyl, lower alkylsilyl, trityl, and lower alkoxytrityl.

5. The process of claim 3 wherein $R_4$ is selected from oxy-loweralkyl, oxyphenyl, oxybenzyl, oxysilyl, oxylower alkylsilyl, oxytrityl and oxy-loweralkoxytrityl, $R_6$ is selected from lower alkyl, phenyl, benzyl, silyl, lower alkylsilyl, trityl, and lower alkoxytrityl and $R_5$ is hydrogen.

* * * * *